United States Patent
Hamada et al.

(10) Patent No.: US 7,919,182 B2
(45) Date of Patent: Apr. 5, 2011

(54) PRESSURE-SENSITIVE ADHESIVE SHEET FOR APPLICATION TO SKIN

(75) Inventors: Atsushi Hamada, Ibaraki (JP); Takashi Kinoshita, Ibaraki (JP); Kenji Furumori, Ibaraki (JP); Kazuhiko Ueda, Kobe (JP); Shintaro Komitsu, Takasago (JP)

(73) Assignees: Nitto Denko Corporation, Ibaraki (JP); Kaneka Corporation, Osaka (JP)

( * ) Notice: Subject to any disclaimer, the term of this patent is extended or adjusted under 35 U.S.C. 154(b) by 992 days.

(21) Appl. No.: 10/574,577

(22) PCT Filed: Sep. 29, 2004

(86) PCT No.: PCT/JP2004/014683
§ 371 (c)(1),
(2), (4) Date: Oct. 10, 2006

(87) PCT Pub. No.: WO2005/032401
PCT Pub. Date: Apr. 14, 2005

(65) Prior Publication Data
US 2008/0311396 A1    Dec. 18, 2008

(30) Foreign Application Priority Data
Oct. 6, 2003  (JP) ................................. 2003-347542

(51) Int. Cl.
*B32B 7/12* (2006.01)
*B32B 15/04* (2006.01)
(52) U.S. Cl. .................................. 428/355 R; 428/343
(58) Field of Classification Search ................. 428/343, 428/355 R
See application file for complete search history.

(56) References Cited

FOREIGN PATENT DOCUMENTS

| | | |
|---|---|---|
| EP | 0 597 636 A1 | 5/1994 |
| JP | 02151677 A * | 6/1990 |
| JP | 4-185687 | 7/1992 |
| JP | 7-33870 | 2/1995 |
| JP | 7-310066 | 11/1995 |
| JP | 2000-302981 | 10/2000 |
| JP | 2002-60456 | 2/2002 |
| JP | 2004-67720 | 3/2004 |

OTHER PUBLICATIONS

English Abstract of JP 02-151677, see above or date and inventor.*
Tsuruo Sakai "Market Prospect for Silicone—Manufacturer Strategy, Application and Development—", CMC Publishing Co., Ltd., Jan. 31, 1990, pp. 89-91, 98 and 99.
Zengyong Chu, New advances of medical pressure-sensitive adhesives, New Chemical Materials, vol. 1, pp. 23-25 (1998) and English translation thereof.
European Communication issued Nov. 17, 2009 in European Patent Application No. 04773614.5-1219.

* cited by examiner

*Primary Examiner* — Victor S Chang
(74) *Attorney, Agent, or Firm* — Wenderoth, Lind & Ponack, L.L.P.

(57) ABSTRACT

The problem of the present invention is to provide a pressure-sensitive adhesive sheet for skin adhesion, having an adhesive layer, which can be formed without using an organic solvent, shows superior adhesion performance to the skin, and shows extremely mild irritation to the skin and stratum corneum damage. To solve the problem, the present invention provides a pressure-sensitive adhesive sheet for skin adhesion, which has a substrate and an adhesive layer laminated on the substrate, wherein the adhesive layer is obtained by curing an adhesive composition containing polyether polymer (A) having at least one alkenyl group on the terminal, compound (B) having 1-10 hydrosilyl groups in a molecule and hydrosilylation catalyst (C).

11 Claims, No Drawings

PRESSURE-SENSITIVE ADHESIVE SHEET FOR APPLICATION TO SKIN

TECHNICAL FIELD

This application is a U.S. National Stage of International Application No. PCT/JP2004/014683, filed Sep. 29, 2004.

The present invention relates to a pressure-sensitive adhesive sheet for skin adhesion, which is used in the medical field.

BACKGROUND ART

Various forms of pressure-sensitive adhesive sheets are used in the medical field, such as surgical tape, adhesive bandage, film dressing materials for wound treatment, a base material for fixing electrode for electrocardiographic measurement and the like. Many of the adhesives used for conventional medical pressure-sensitive adhesive sheets are made of acrylic polymers. Acrylic polymer is generally applied, for example, to a supportive substrate and release paper after adjusting viscosity with an organic solvent and the like. The organic solvent used for adjusting the viscosity is removed by volatilization after application. In so doing, the organic solvent is sometimes not removed sufficiently (insufficient drying), and the organic solvent may remain in the adhesive. When a pressure-sensitive adhesive sheet having a constitution where an adhesive directly touches the human body, such as an adhesive bandage and the like, is not dried sufficiently, the organic solvent remaining in the adhesive, which is absorbed into the body from the skin, may cause inflammation such as exanthema and the like. In addition, the organic solvent removed in the drying step is feared to cause environmental pollution and endanger the health and safety of the workers.

As a production method of conventional solvent-free pressure-sensitive adhesive tapes, a hotmelt method comprising heating, kneading and/or melting an adhesive for hotmelt and applying the same to a substrate, an emulsion method comprising applying an emulsion adhesive to a substrate and drying the same, an extrusion polymerization method comprising extruding a thermally polymerizable monomer liquid on a substrate while heating, kneading and polymerizing in a heating barrel, a photopolymerization method comprising applying a photopolymerizable monomer liquid to a substrate and exposing the same to light irradiation in an inert atmosphere to allow polymerization and the like are known. They are unsatisfactory from the viewpoints of workability (introduction into apparatus for light irradiation, reaction time), cost and the like, and from the viewpoints of adhesion performance such as adhesion to the skin, irritation, glue remainder and the like, and no production method can be preferably used for medical pressure-sensitive adhesive sheets such as adhesive bandage and the like.

As one embodiment of solvent-free adhesives, adhesives using urethane crosslinking, which use an oxyalkylene polymer, are known (JP-A-7-310066, JP-A-2002-60456). The aforementioned adhesives have been reported to be superior in adhesion to the skin, moisture permeability, water absorbability and the like. However, the adhesive is associated with problems in that the curing speed is difficult to control because of urethane crosslinking, and unreacted isocyanate has toxicity.

DISCLOSURE OF THE INVENTION

It is therefore an object of the present invention to provide a pressure-sensitive adhesive sheet for skin adhesion, that can be formed without using an organic solvent, can be easily adhered to the skin, does not irritate the skin easily, and that does not damage stratum corneum easily.

The present inventors have conducted intensive studies in an attempt to solve the aforementioned problems and completed the present invention having the following characteristics.

[1] A pressure-sensitive adhesive sheet for skin adhesion, which comprises a substrate and an adhesive layer laminated on the aforementioned substrate, wherein
the adhesive layer is obtained by curing an adhesive composition comprising polyether polymer (A) having at least one alkenyl group on the terminal, compound (B) having 1-10 hydrosilyl groups in a molecule and hydrosilylation catalyst (C).

[2] The pressure-sensitive adhesive sheet of [1], wherein the polymer (A) is a polyether polymer having an alkenyl group represented by the following formula (1) or (2),

$$H_2C=C(R^1)— \quad (1)$$

$$HC(R^1)=CH— \quad (2)$$

wherein $R^1$ is a hydrogen atom or a hydrocarbon group having 1 to 10 carbon atoms, and
the catalyst (C) is a platinum complex that does not contain a conjugate base of a strong acid as a ligand.

[3] The pressure-sensitive adhesive sheet of [2], wherein $R^1$ is a hydrogen atom or a methyl group.

[4] The pressure-sensitive adhesive sheet of [2] or [3], wherein the above-mentioned platinum complex is a platinum-vinyl siloxane complex.

[5] The pressure-sensitive adhesive sheet of [4], wherein the platinum-vinyl siloxane complex is a platinum-1,3-divinyl-1,1,3,3-tetramethyldisiloxane complex or a platinum-1,3,5,7-tetravinyl-1,3,5,7-tetramethylcyclotetrasiloxane complex.

[6] The pressure-sensitive adhesive sheet of any of [1] to [5], wherein the main chain of the polymer (A) has a polyoxypropylene skeleton.

[7] The pressure-sensitive adhesive sheet of any of [1] to [6], wherein the polymer (A) has a number average molecular weight in polystyrene conversion of 3000-50000 as measured by size-exclusion chromatography.

[8] The pressure-sensitive adhesive sheet of any of [1] to [7], wherein the proportion of the toluene-insoluble component in the adhesive layer is 10-50 wt %.

[9] The pressure-sensitive adhesive sheet of any of [1] to [8], which has a moisture permeability of not less than 800 g/m$^2$·24 hr, as measured under the conditions of thickness of adhesive layer 50 μm, temperature 40° C. and relative humidity 30%.

DETAILED DESCRIPTION OF THE INVENTION

The pressure-sensitive adhesive sheet of the present invention has a substrate and an adhesive layer. Of these, the adhesive layer is obtained by curing an adhesive composition comprising the above-mentioned polymer (A), compound (B) and catalyst (C).

Polymer (A) is a polyether polymer having at least one alkenyl group on the terminal. The alkenyl group is not particularly limited as long as it contains a carbon-carbon double bond active for a hydrosilylation reaction. As the alkenyl group, an aliphatic unsaturated hydrocarbon group preferably having 2-20, more preferably 2-4, carbon atoms (e.g., vinyl group, allyl group, methylvinyl group, propenyl group, butenyl group, pentenyl group, hexenyl group etc.), a cyclic unsaturated hydrocarbon group preferably having 3-20, more preferably 3-6, carbon atoms (e.g., cyclopropenyl group, cyclobutenyl group, cyclopentenyl group, cyclohexenyl group etc.), methacrylic group and the like can be mentioned.

Since synthesis reaction can be easily carried out, a preferable alkenyl group is a group represented by the following formulas (1) and (2). In the following formulas, $R^1$ is a hydrogen atom or a hydrocarbon group having 1 to 10 carbon atoms, with preference given to a hydrogen atom and a methyl group.

 (1)

 (2)

The polymer (A) has at least one, preferably 1-5, more preferably 1-3, still more preferably 1-2, alkenyl groups in one molecule (polymer) on average. When the number of alkenyl groups in 1 molecule of polymer (A) is less than one on average, curing becomes difficult, and when the number of alkenyl groups contained in 1 molecule is too high, the network structure becomes dense and the adhesive property tends to be degraded.

As a typical example of polyether polymer, which is the basic skeleton of polymer (A), a polyoxyalkylene polymer comprising a repeating unit represented by the formula ($-R^2-O-$) can be mentioned, wherein $R^2$ is a divalent alkylene group. In view of easy availability and easy handling, the main chain of preferable polymer (A) has a polyoxypropylene skeleton. In other words, the above-mentioned $R^2$ is preferably $-CH_2CH(CH_3)-$. The polyether polymer may be made of one kind of repeating unit or multiple repeating units. The polyether polymer may be a linear polymer or branched polymer.

While the whole polymer (A) other than the alkenyl group is preferably made of a polyether skeleton, other structure unit may also be contained. In this case, the total proportion of the polyether skeleton in polymer (A) is preferably not less than 80 wt %, more preferably not less than 90 wt %.

In view of easy operation at room temperature, and superior adhesive property, the number average molecular weight of polymer (A) is preferably 3000-50000, more preferably 6000-50000, and particularly preferably 10000-30000. When the number average molecular weight is less than 3000, the obtained cured product tends to become brittle, and when the number average molecular weight exceeds 50000, the adhesive composition becomes highly viscous and difficult to handle. The above-mentioned number average molecular weight is a number average molecular weight based on polystyrene, as measured by size-exclusion chromatography.

The binding mode of the alkenyl group to a polyether polymer is not particularly limited. As the bond between the alkenyl group and the polyether polymer, a direct bond, an ether bond, an ester bond, a carbonate bond, a urethane bond, a urea bond and the like can be mentioned.

The production method of polymer (A) is not particularly limited and, for example, a method comprising producing a polyether polymer and then introducing an alkenyl group thereinto can be mentioned. In this case, various known production methods can be adopted for the polyether polymer, or, commercially available polyether polymer may be used. The method for introducing an alkenyl group into a polyether polymer is also known and, for example, a method of copolymerizing a monomer having an alkenyl group (e.g., allylglycidylether) and a monomer for synthesizing a polyether polymer, a method comprising reacting a polyether polymer wherein a functional group (e.g., hydroxyl group, alkoxide group) has been introduced in advance into a desired part (main chain terminal etc.) with a compound having both a functional group reactive with the functional group and an alkenyl group (e.g., acrylic acid, methacrylic acid, vinyl acetate, acrylic acid chloride etc.) and the like can be mentioned.

The compound (B) has 1-10 hydrosilyl groups in a molecule. The hydrosilyl group means a group having a Si—H bond. In the present invention, when two hydrogen atoms (H) are bonded to one silicon atom (Si), two hydrosilyl groups are considered to be present. The chemical structure of compound (B) other than the hydrosilyl group is not particularly limited. The number average molecular weight of compound (B) as calculated from the SiH group value measured from the amount of generated hydrogen is preferably 400-3000, more preferably 500-1000. When the number average molecular weight is too low, volatilization easily occur during heat-curing, and cured product is difficult to obtain, and when it is too high, the curing rate tends to be low.

The number of hydrosilyl groups contained in one molecule of compound (B) is 1-10, preferably 2-8. When compound (B) has not less than 2 hydrosilyl groups, multiple polymers (A) can be crosslinked during cure and the resulting pressure-sensitive adhesive sheet expresses a preferable cohesion force. As a result, glue remainder and the like do not occur easily when the pressure-sensitive adhesive sheet is adhered to the skin and peeled off thereafter. However, when the number of hydrosilyl groups is too many, the crosslinking becomes too dense, and the obtained pressure-sensitive adhesive sheet tends to show degraded adhesive property such as adhesion to the skin, tacky feeling and the like. Furthermore, the stability of compound (B) becomes poor, a large amount of hydrosilyl group remains after curing in the cured product to possibly cause irritation to the skin and voids. The level of density of crosslinking greatly affects the level of density of the main chain polyether parts of polymer (A), which in turn affects the moisture permeability of the pressure-sensitive adhesive sheet as a whole. Thus, the number of hydrosilyl groups of compound (B) should be determined in consideration of the balance between the moisture permeability and the adhesive property. Compound (B) may be used alone or in combination of two or more kinds thereof. It is preferable that compound (B) be highly compatible with polymer (A).

In view of easy availability of starting materials and compatibility with polymer (A), preferable compound (B) is organohydrogen siloxane modified with an organic group. A typical example of organohydrogen siloxane is a compound represented by the following formula (3):

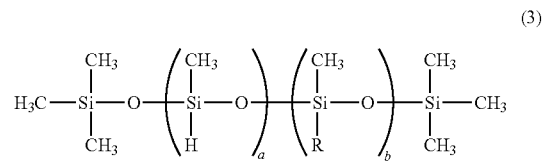 (3)

The value of a in the formula (3) corresponds to the number of hydrosilyl group in one molecule. While the value of a+b is not particularly limited, it is preferably 2-50, more preferably 2-20. In the formula, R is a hydrocarbon group having 2-20 (preferably 4-12) carbon atoms in the main chain, which is specifically a monovalent residue obtained by cleaving the double bond of the below-mentioned organic compound (allyl compound). The compound of the formula (3) can be obtained by modifying unmodified methylhydrogensilicone to introduce a hydrocarbon group R. The unmodified methylhydrogensilicone corresponds to a compound of the formula (3) wherein each R is H, and is used as a starting material for various modified silicones, as described in "Market Prospect for Silicone—Manufacturer Strategy, Application and Development—", CMC Publishing CO., LTD. (1990.1.31). As the organic compound (allyl compound) used for introduction of R, α-olefin, styrene, α-methylstyrene, allyl alkyl ether, allyl alkyl ester, allyl phenyl ether, allyl phenyl ester and the like can be mentioned. The number of hydrosilyl groups that the modified molecule has can be controlled by the amount of the aforementioned organic compound to be added for modification (see Examples).

The amount ratio of polymer (A) and compound (B) in the adhesive composition used for forming an adhesive layer is expressed by the ratio of the total amount of the hydrosilyl group derived from compound (B) to the total amount of the alkenyl group derived from polymer (A). The level of crosslinking density after curing is determined by the total amount of hydrosilyl group per 1 mol of the total amount of the alkenyl group in the adhesive composition. In consideration of the balance between appropriate adhesiveness and small glue remainder and the like, the total amount of hydrosilyl group per 1 mol of the total amount of alkenyl group is preferably 0.3-0.8 mol, more preferably 0.4-0.7 mol.

The catalyst (C), i.e., hydrosilylation catalyst, is not particularly limited, and any can be used as long as it promotes the hydrosilylation reaction. Specifically, chloroplatinic acid, platinum-vinylsiloxane complexes (e.g., platinum-1,3-divinyl-1,1,3,3-tetramethyldisiloxane complex, platinum-1,3,5,7-tetravinyl-1,3,5,7-tetramethylcyclotetrasiloxane complex), platinum-olefin complexes (e.g., $Pt_x(ViMe_2SiOSiMe_2Vi)_y$, $Pt[(MeViSiO)_4]_z$ (wherein x, y and z are each a positive integer)) and the like can be mentioned. Of these, from the aspect of catalyst activity, a platinum complex catalyst free of a conjugate base of a strong acid as a ligand is preferable, platinum-vinylsiloxane complex is more preferable, and platinum-1,3-divinyl-1,1,3,3-tetramethyldisiloxane complex and platinum-1,3,5,7-tetravinyl-1,3,5,7-tetramethylcyclotetrasiloxane complex are particularly preferable.

The amount of catalyst (C) is not particularly limited, and it is preferably $10^{-8}$-$10^{-1}$ mol, more preferably $10^{-6}$-$10^{-3}$ mol, per 1 mol of alkenyl group of polymer (A) in the adhesive composition. When the amount is within the above-mentioned range, appropriate curing rate, stable curability, ensured pot life as requested and the like can be easily achieved.

The adhesive composition may contain components other than the above-mentioned (A)-(C). As such component, tackifier, adhesive additive, storage stabilizer for compound (B), and other components can be mentioned.

As the tackifier and adhesive additive, phenolic resin, modified phenolic resin, terpene phenol resin, xylene phenol resin, cyclopentadiene-phenol resin, xylene resin, petroleum resin, phenol-modified petroleum resin, rosin ester resin, low molecular weight polystyrene resin, terpene resin and the like can be mentioned. When these are used to improve adhesive property, they may be used alone or in combination of two or more kinds thereof. The amount of these tackifiers and adhesive additives is preferably 10-100 parts by weight, more preferably 15-50 parts by weight, per 100 parts by weight of the total amount of polymer (A) and compound (B). When the amount used is too high, the adhesive layer unpreferably shows degraded moisture permeability.

As the storage stabilizer for compound (B), aliphatic compound having an unsaturated bond, organic phosphorus compound, organic sulfur compound, nitrogen-containing compound, tin compound, organic peroxide and the like can be mentioned, which provide an effect of improving the pot life of an adhesive composition.

The adhesive composition used for forming an adhesive layer may contain a water-soluble organic polymer or a water absorbable polymer for improving water resistance, sweat resistance, water absorbability and the like of the adhesive layer. Moreover, other plasticizer, softening agent, filler, pigment, surfactant, UV absorber, antioxidant, antibacterial agent and the like may be further added. While the use of an organic solvent here is not preferable, the use thereof is not entirely denied.

The adhesive layer of the pressure-sensitive adhesive sheet of the present invention can be obtained by curing the aforementioned adhesive composition. The curing here means a hydrosilylation reaction between polymer (A) and compound (B) by heating. The cure conditions include, for example, standing at 40-180° C. for 1-60 min. To make curing more complete, the adhesive composition may be left standing at 40-80° C. for several days. The level of curing can be expressed by the proportion (wt %) of the toluene-insoluble component in the adhesive layer. The toluene-insoluble component refers to a component insoluble even after immersion in toluene for 7 days. The specific test steps to determine the above-mentioned proportion is described in the following Examples. Preferably, the proportion of the toluene-insoluble component in the adhesive layer is 10-50 wt %. When the proportion is within this range, cohesive failure does not occur easily whether or not the adhesive composition is completely cured. The cohesive failure here means adhesive remainder on the skin when the obtained pressure-sensitive adhesive sheet is adhered to the skin and then peeled off. The amount of the toluene-insoluble component can be controlled by the amount ratio of the aforementioned polymer (A) and compound (B) (ratio of the total amount of alkenyl group and the total amount of hydrosilyl group) and cure conditions.

The viscosity during curing is preferably 10-1000 Pa·s. The viscosity can be controlled by the amount ratio of components (A)-(C) and the kind and amount of the aforementioned storage stabilizer for compound (B). To increase the viscosity, for example, the following means can be mentioned.

To lower the temperature of the adhesive composition to be applied.

To allow pre-gelation of polymer (A) by adding a small amount of compound (B).

The substrate to be used for the pressure-sensitive adhesive sheet of the present invention is not particularly limited as long as it can hold an adhesive composition before curing. The materials of the substrate include urethane polymers such as polyetherurethane and the like, amide polymers such as polyetheramide and the like, acrylic polymers such as polyacrylate and the like, olefin polymers such as polyethylene, polypropylene, ethylene-vinyl acetate copolymer and the like, ester polymers such as polyether polyester and the like, and the like. The substrate may be a single layer or a laminate comprising multiple layers. In the case of a laminate, the layers may be made of the same material or different kinds of materials. It is preferable to select the material of a substrate from fabric such as non-woven fabric, woven fabric and the like, and vapor permeable polymer sheet, to prevent getting sweaty and the like during application to the skin. For the same reasons, the substrate may be appropriately perforated. The thickness of the substrate is not particularly limited, and can be appropriately determined according to the object and use. It is, for example, 10-5000 μm. The pressure-sensitive adhesive sheet of the present invention widely encompasses the sheets having an about plate shape, and includes not only the "sheet" but also those that can be referred to as a "film".

A method of forming an adhesive layer on a substrate is not particularly limited and, for example, a method comprising applying an adhesive composition to one surface of the substrate and curing same under the aforementioned conditions, and a method comprising applying a releasing agent to a sheet (release sheet) in advance, applying an adhesive composition, curing and adhering the sheet to a substrate can be mentioned. As the releasing agent, various silicone, olefin or fluorine releasing agents and the like are known, which can be used appropriately. Of these, olefin releasing agents and non-solvent addition curing type silicone releasing agents are preferable from the aspects of cost and ensured release property.

The thickness of the adhesive layer is not particularly limited, and it is, for example, 10-5000 μm.

The pressure-sensitive adhesive sheet for skin adhesion of the present invention preferably shows a tensile stress of 0.3-3.0 N/20 mm, more preferably 0.6-1.5 N/20 mm, after adhesion to the skin (back) of human body, and peeling off 6 hr later at a peeling rate of 300 mm/min and at a peeling angle of 180 degrees. In addition, the area ratio of detached stratum corneum upon peeling off is preferably not more than 30%, more preferably 0-10%. When the tensile stress caused by peeling off from the skin is within the above range, the adhesive sheet has sufficient skin adhesive force, and can be peeled off without damaging the skin. In addition, it shows a sufficient adhesive force even after repeated adhesion. To improve the above-mentioned tensile stress, the molecular weight between crosslinks of the adhesive may be increased, the crosslinking density may be decreased, the moisture permeability of the pressure-sensitive adhesive sheet as a whole may be raised and the like. The above-mentioned tensile stress can be decreased by performing conversely. To decrease the above-mentioned area ratio of detached stratum corneum, the moisture permeability of the pressure-sensitive adhesive sheet as a whole may be increased, the crosslinking density may be increased, and the like.

The pressure-sensitive adhesive sheet for skin adhesion of the present invention has a moisture permeability of not less than 800 g/m²·24 hr, more preferably 800-3000 g/m²·24 hr, as measured under the conditions of thickness of adhesive layer 50 μm, temperature 40° C. and relative humidity 30%. When the moisture permeability of the pressure-sensitive adhesive sheet as a whole is within this range, sweatiness and irritation to the skin from adhesion for a long time can be prevented. The specific measurement method of the moisture permeability is mentioned below. While the moisture permeability of the pressure-sensitive adhesive sheet naturally depends on the material and structure of the substrate and the like, the use of the aforementioned adhesive composition expands the range of choices for the substrate that affords the above-mentioned preferable moisture permeability. To improve the moisture permeability of the pressure-sensitive adhesive sheet, crosslinking density of the adhesive may be increased, the proportion of polyether unit in polymer (A) may be increased and the like.

The pressure-sensitive adhesive sheet "for skin adhesion" refers to sheet in general, which is adhered to the skin for the prophylaxis or treatment of illness or wounds, diagnosis of health condition, fixing a catheter and the like to the skin surface and the like. The pressure-sensitive adhesive sheet may or may not further contain a medicinal ingredient. Specific examples of the pressure-sensitive adhesive sheet for skin adhesion include, but are not limited to, surgical tape, adhesive bandage, film dressing materials for wound treatment, a base material for fixing electrode for electrocardiographic measurement and the like.

EXAMPLES

The present invention is explained in detail in the following by referring to Examples, which are not to be construed as limitative. Various modifications and changes may be made to the present invention without departing from the technical scope of the invention.
(Synthesis of Polymer A-1)

By polymerization using a mixed metal cyanide complex (zinc hexacyano cobaltate) and caustic alkali as a catalyst, polyoxypropylene glycol having a number average molecular weight of 3000 was obtained. Using the polyoxypropylene glycol as an initiator, propylene oxide was polymerized to give an oxypropylene polymer. The oxypropylene polymer was applied to the method of Synthetic Example 1 of JP-A-5-117521 to give a polymer having a number average molecular weight of 28000. The terminal of the polymer was converted to an allyl group using a 28% methanol solution of sodium methylate and allyl chloride, and the polymer was purified by desalting to give a polyoxyalkylene polymer (polymer A-1) generally having two terminal allyl groups in one molecule. The amount of the terminal allyl group of the obtained polymer was 0.12 mmol/g.
(Synthesis of Polymer A-2)

By polymerization according to the method of JP-A-5-117521, comparative Synthetic Example 1, using caustic alkali as a catalyst, polyoxypropylene glycol having a number average molecular weight of 3000 was obtained. This polyoxypropylene glycol, alkali and dihalomethane were subjected to a molecular chain extension reaction, the terminal was converted to an allyl group with allyl chloride, and the polymer was purified by desalting to give polymer A-2. The number average molecular weight of this polymer by GPC was 13800 and the polymer generally had two terminal allyl groups in one molecule. The amount of the terminal allyl group relative to the weight of polymer A-2 was 0.24 mmol/g.
(Synthesis of compound B-1)

To methylhydrogensilicone represented by the following formula (4) wherein x is 5 on average was added, in the presence of a platinum catalyst, α-methylstyrene in an amount of 0.6 equivalent relative to the amount of entire hydrosilyl group to give a compound (compound B-1) generally having two terminal allyl groups in one molecule. The hydrosilyl group content of this compound was 2.5 mmol/g.

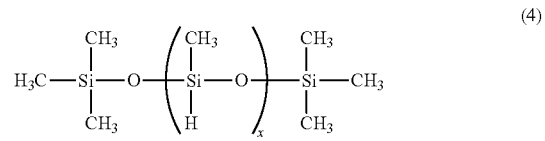

(4)

(Synthesis of Compound B-2)

To methylhydrogensilicone represented by the formula (4) wherein x is 5 on average was added, in the presence of a platinum catalyst, α-methylstyrene in an amount of 0.4 equivalent relative to the amount of entire hydrosilyl group to give a compound (compound B-2) generally having three terminal allyl groups in one molecule. The hydrosilyl group content of this compound was 4.1 mmol/g.
(Synthesis of Compound B-3)

To methylhydrogensilicone represented by the formula (4) wherein x is 10 on average was added, in the presence of a platinum catalyst, α-methylstyrene in an amount of 0.5 equivalent relative to the amount of entire hydrosilyl group to give a compound (compound B-3) generally having five terminal allyl groups in one molecule. The hydrosilyl group content of this compound was 4.2 mmol/g.

Examples 1-12

To a given amount of polymer A-1 or A-2 was added a given amount of compound B-1, B-2 or B-3 (combination and amount thereof are shown in Table 1). The mixtures were thoroughly mixed with 100 μl of a platinum-1,3-divinyl-1,1,3,3-tetramethyldisiloxane complex (hydrosilylation catalyst, 3 wt %, platinum isopropanol solution) and 23 mg of dimethyl maleate to give adhesive compositions. The adhesive compositions were applied, at room temperature, to the treated surface of a release paper subjected to a silicone release treatment, such that the thickness after curing became 50 μm, and the release paper was cured at 130° C. for 3 min to give an adhesive layer. Then, a polyester non-woven fabric (grammage 35 g/m$^2$) was laminated on the cured adhesive layer as a substrate under the conditions of 120° C., 5 kg/cm$^2$, rate 2 m/min. In this way, pressure-sensitive adhesive sheets were prepared.

Comparative Example 1

Isononyl acrylate (65 parts), 2-methoxyethyl acrylate (30 parts) and acrylic acid (5 parts) were copolymerized and the obtained acrylic copolymer (100 parts) was dissolved in toluene (200 parts) to give a homogeneous solution of a medical adhesive. The solution was applied to the treated surface of a release sheet subjected to a release treatment, such that the thickness after curing became 50 μm, and the release paper was dried at 110° C. for 3 min and transferred to a non-woven fabric (same as the above-mentioned Example) as a substrate to give a pressure-sensitive adhesive sheet.

TABLE 1

| | polymer (A) (kind, g) | compound (B) (kind, g) | SiH group/ allyl group (molar ratio) | tackifier resin (g) |
|---|---|---|---|---|
| Ex. 1 | A-1, 100 | B-1, 2.4 | 0.5 | 0 |
| Ex. 2 | A-1, 100 | B-1, 2.9 | 0.6 | 0 |
| Ex. 3 | A-1, 100 | B-1, 3.4 | 0.7 | 20 |
| Ex. 4 | A-1, 100 | B-2, 1.5 | 0.5 | 0 |
| Ex. 5 | A-1, 100 | B-2, 1.8 | 0.6 | 0 |
| Ex. 6 | A-1, 100 | B-2, 2.1 | 0.7 | 20 |
| Ex. 7 | A-1, 100 | B-3, 1.4 | 0.5 | 0 |
| Ex. 8 | A-1, 100 | B-3, 1.7 | 0.6 | 0 |
| Ex. 9 | A-1, 100 | B-3, 2.0 | 0.7 | 20 |
| Ex. 10 | A-2, 100 | B-1, 4.9 | 0.5 | 40 |
| Ex. 11 | A-2, 100 | B-2, 3.0 | 0.5 | 40 |
| Ex. 12 | A-2, 100 | B-3, 2.9 | 0.5 | 40 |
| Com. Ex. 1 | (acrylic) | | | |

(Proportion of Solvent (Toluene) Insoluble Component in Adhesive Layer)

An adhesive (0.5 g) was taken from each pressure-sensitive adhesive sheet, and the weight ($W_1$) was precisely measured. The sample was extracted with toluene (50 g) at ambient temperature for 7 days, and the residue (toluene-insoluble content) was filtered through a polytetrafluoroethylene porous membrane (average pore size 0.2 μm, manufactured by Nitto Denko Corporation, NTF membrane) and dried. The weight ($W_2$) of the dried adhesive was precisely measured, and the solvent (toluene)-insoluble content (wt %) was determined. Solvent-insoluble content (wt %)=($W_2 \times 100$)/($W_1$)

(Skin Adhesive Force (Tensile Stress))

A pressure-sensitive adhesive sheet cut into a 20 mm width was adhered to the back of five volunteers, and press-adhered with one reciprocation of a roller weighing 1 kg. After 6 hr, the pressure-sensitive adhesive sheet was peeled off, and the release force (tensile stress) then was measured. The tensile stress (N/20 mm) was measured using a tensile tester "Autograph AGS-100D" manufactured by Shimadzu Corporation under the conditions of room temperature (23° C.), relative humidity 65%, tensile speed 300 mm/min, release angle 180°. The average value of the tensile stress of five volunteers was calculated. In addition, the destruction of the adhesive layer after peeling off was visually observed to determine whether it was cohesive failure or interfacial fracture.

(Moisture Permeability)

Distilled water (10 ml) was placed in a cylindrical glass container (inner diameter 40 mm, height 40 mm) and to the opening of the container was adhered and fixed a round pressure-sensitive adhesive sheet cut into a circle (diameter 50 mm), with the adhesive layer facing down. The weight ($W_3$) of the whole container with the pressure-sensitive adhesive sheet was measured, and the container was placed in a thermo-hygrostat at 40° C., relative humidity 30% and stood for 24 hr. The weight ($W_4$) after the lapse of 24 hr was measured and the moisture permeability was calculated from the following formula.

Moisture permeability (g/m$^2 \cdot$24 h)=($W_3 - W_4$)/(0.02×0.02×π)

(Skin Irritation)

With the pressure-sensitive adhesive sheet after peeling off, which was used for the measurement of the skin adhesive force, stratum corneum detach amount was measured. Specifically, the sample sheets peeled off from the back of the volunteers were immersed in a stratum corneum staining solution (Gentian Violet 1%, Brilliant Green 0.5%, distilled water 98.5%) manufactured by Wako Pure Chemical Industries, Ltd. for about 30 min to allow coloring of skin stratum corneum. Thereafter, the pressure-sensitive adhesive sheet was sufficiently washed with distilled water and dried for 24 hr. The adhesive layer of the dried pressure-sensitive adhesive sheet was observed with a microscope, the images were analyzed and the area ratio of the detached stratum corneum was determined. The area ratio of damaged stratum corneum was an average of five volunteers.

The measurement results of each pressure-sensitive adhesive sheet are summarized in Table 2.

TABLE 2

| | toluene insoluble component (wt %) | moisture permeability (g/m$^2 \cdot$ 24 h) | skin adhesive force (state of destruction N/20 mm) | area ratio (%) of damaged stratum corneum |
|---|---|---|---|---|
| Ex. 1 | 20 | 1000 | interface, 1.3 | 10 |
| Ex. 2 | 25 | 900 | interface, 1.1 | 10 |
| Ex. 3 | 30 | 1000 | interface, 0.5 | 5 |
| Ex. 4 | 25 | 900 | interface, 1.1 | 10 |
| Ex. 5 | 30 | 1000 | interface, 0.5 | 10 |
| Ex. 6 | 35 | 1000 | interface, | 10 |

TABLE 2-continued

|  | toluene insoluble component (wt %) | moisture permeability (g/m² · 24 h) | skin adhesive force (state of destruction N/20 mm) | area ratio (%) of damaged stratum corneum |
|---|---|---|---|---|
| Ex. 7 | 20 | 1500 | 0.5 interface, 0.5 | 5 |
| Ex. 8 | 25 | 1100 | interface, 0.4 | 5 |
| Ex. 9 | 30 | 1000 | interface, 0.4 | 5 |
| Ex. 10 | 25 | 1200 | interface, 0.4 | 10 |
| Ex. 11 | 30 | 1200 | interface, 0.4 | 10 |
| Ex. 12 | 30 | 1800 | interface, 0.4 | 10 |
| Com. Ex. 1 | 0 | 400 | interface, 1.5 | 80 |

INDUSTRIAL APPLICABILITY

The pressure-sensitive adhesive sheet of the present invention shows superior adhesive property. That is, even if additives other than the main polymers, such as tackifier resin, softening agent, water absorbable resin and the like, are not used as adhesive components, or are used in reduced amounts, the pressure-sensitive adhesive sheet of the present invention shows superior adhesion performance. The substrate to be used for the pressure-sensitive adhesive sheet of the present invention can be freely selected depending on the use, from those having or not having moisture permeability.

This application is based on a patent application No. 2003-347542 filed in Japan, the contents of which are hereby incorporated by reference.

The invention claimed is:

1. A pressure-sensitive adhesive sheet for skin adhesion, which comprises a substrate and an adhesive layer laminated on the substrate, wherein the adhesive layer is obtained by curing an adhesive composition comprising polyether polymer (A) having a number average molecular weight of 10000-30000 and at least one alkenyl group on the terminal, compound (B) having a number average molecular weight of 500-1000 and 1-10 hydrosilyl groups in a molecule and hydrosilylation catalyst (C), and the molar ratio of the hydrosilyl group/alkenyl group is 0.3-0.8.

2. The pressure-sensitive adhesive sheet of claim 1, wherein the polymer (A) is a polyether polymer having an alkenyl group represented by the following formula (1) or (2), $$H_2C=C(R^1)- \quad (1)$$

$$HC(R^1)=CH- \quad (2)$$

wherein $R^1$ is a hydrogen atom or a hydrocarbon group having 1 to 10 carbon atoms, and the catalyst (C) is a platinum complex that does not contain a conjugate base of a strong acid as a ligand.

3. The pressure-sensitive adhesive sheet of claim 2, wherein $R^1$ is a hydrogen atom or a methyl group.

4. The pressure-sensitive adhesive sheet of claim 2, wherein the platinum complex is a platinum-vinyl siloxane complex.

5. The pressure-sensitive adhesive sheet of claim 4, wherein the platinum-vinyl siloxane complex is a platinum-1,3-divinyl-1,1,3,3-tetramethyldisiloxane complex or a platinum-1,3,5,7-tetravinyl-1,3,5,7-tetramethylcyclotetrasiloxane complex.

6. The pressure-sensitive adhesive sheet of claim 1, wherein the main chain of the polymer (A) has a polyoxypropylene skeleton.

7. The pressure-sensitive adhesive sheet of claim 1, wherein the polymer (A) has a number average molecular weight in polystyrene conversion of 3000-50000 as measured by size-exclusion chromatography.

8. The pressure-sensitive adhesive sheet of claim 1, wherein the proportion of the toluene-insoluble component in the adhesive layer is 10-50 wt %.

9. The pressure-sensitive adhesive sheet of claim 1, which has a moisture permeability of not less than 800 g/m²·24 hr, as measured under the conditions of thickness of adhesive layer 50 μm, temperature 40° C. and relative humidity 30%.

10. The pressure-sensitive adhesive sheet of claim 3, wherein the platinum complex is a platinum-vinyl siloxane complex.

11. The pressure-sensitive adhesive sheet of claim 10, wherein the platinum-vinyl siloxane complex is a platinum-1,3-divinyl-1,1,3,3-tetramethyldisiloxane complex or a platinum-1,3,5,7-tetravinyl-1,3,5,7-tetramethylcyclotetrasiloxane complex.

* * * * *